United States Patent [19]

Tillotson

[11] Patent Number: 5,053,626

[45] Date of Patent: Oct. 1, 1991

[54] DUAL WAVELENGTH SPECTROFLUOROMETER

[75] Inventor: Douglas L. Tillotson, Milton, Mass.

[73] Assignee: Boston University, Boston, Mass.

[21] Appl. No.: 414,755

[22] Filed: Sep. 29, 1989

[51] Int. Cl.$^5$ .............................................. G01N 21/64
[52] U.S. Cl. ............................ 250/458.1; 250/459.1; 356/417
[58] Field of Search ............... 250/458.1, 459.1, 461.1, 250/461.2; 356/417, 317, 73

[56] References Cited

U.S. PATENT DOCUMENTS

| | | | |
|---|---|---|---|
| 2,758,502 | 8/1956 | Scott et al. | 88/14 |
| 2,986,066 | 5/1961 | Rouy | 88/14 |
| 3,819,277 | 6/1974 | Berthelot et al. | 356/204 |
| 3,887,281 | 6/1975 | Kurita et al. | 356/96 |
| 4,153,369 | 5/1979 | Kallet et al. | 356/318 |
| 4,524,383 | 6/1985 | de Rooij | 358/55 |
| 4,573,195 | 2/1986 | de France | 382/6 |
| 4,631,582 | 12/1986 | Nagasaki et al. | 358/98 |
| 4,636,068 | 1/1987 | Niiho et al. | 356/5 |
| 4,729,018 | 3/1988 | Watanabe et al. | 358/98 |
| 4,744,667 | 5/1988 | Fay et al. | 356/417 |
| 4,821,117 | 4/1989 | Sekiguchi | 358/98 |
| 4,859,063 | 8/1989 | Fay et al. | 356/418 |

OTHER PUBLICATIONS

*Calcium Response of Single Adrenal Glomerulosa Cells to External Potassium*, by S. J. Quinn, G. H. Williams and D. L. Tillotson, (1988), pp. E488-E495.

*Primary Examiner*—Jack I. Berman
*Assistant Examiner*—Richard Hanig
*Attorney, Agent, or Firm*—Hamilton, Brook, Smith & Reynolds

[57] ABSTRACT

A spectrofluorometry apparatus utilizes dual wavelengths. The dual wavelengths are produced using different wavelength filters and a rotating reflective disk that direct the light to each of the respective filters. The reflective disk contains a notch that allows light to pass through it and two reflective surfaces that reflect light. As the disk rotates, the light is appropriately distributed to the respective filters. The rotation of the reflective disk is synchronized to a video camera that is used to image fluorescence. The camera is designed so that each of the wavelengths are giving alternating video frames.

47 Claims, 6 Drawing Sheets

DUAL WAVELENGTH SPECTROFLUOROMETER

BACKGROUND OF THE INVENTION

A material can often be characterized by the response of a fluorescent probe to radiation. In some procedures, a sample is illuminated alternately with light of different wavelengths, and the fluorescence of the sample with the different illuminating wavelengths is noted. For example, the calcium ion is believed to control a variety of cellular processes with a high degree of spatial and temporal precision. Calcium has been measured in single living cells with high spatial resolution utilizing a microscope and a highly fluorescent calcium sensitive dye Fura-2. A sample to which the dye has been added is illuminated alternately with light of 340 and 380 nanometers. The free fluorescent dye fluoresces at about 500 nanometers maximally in response to the 380 nanometers excitation; whereas, the dye associated with the calcium ion fluoresces at about 500 nanometers maximally in response to the 340 nanometer excitation. The concentration of calcium can then be calculated from the formula:

$$[Ca^{++}]i = K_d[(R-R_{min})/(R_{max}-R)]\beta$$

Where $K_d$ is the effective dissociation constant for the Fura-2-Calcium reaction. R is the measured ratio of fluorescent intensity at 500 nm with the 340 and 380 nm excitation, $R_{min}$ is the limiting value of R at a calcium concentration of zero, $R_{max}$ is R with fully saturated calcium and $\beta$ an optical constant for the system which is a measure of the relative quantum yield at 380 nm of the calcium free and calcium saturated dye. It is assumed that each of the parameters is corrected for background intensity.

SUMMARY OF THE INVENTION

A microscope system is comprised of a means for locating a sample and a source of radiation for illuminating a sample. A detector is positioned so as to detect radiation resulting from the illumination of the sample by the source of radiation. The source of radiation may be a light source in the ultraviolet range such as a xenon light source. One particular type of xenon light source that works well is a xenon arc bulb. Such sources of radiation produce fluorescence in a sample which is detected by the detector. The detector may be either a photomultiplier tube or a video camera.

The microscope includes a filtering assembly that is located in the optical path of the radiation. The filtering assembly may be located at either the portion of the path from the source of radiation to the sample or in the portion of the path from the sample to the detector. In either event, the filtering assembly is comprised of a first filter and a second filter. Both of these filters remove all wavelengths from the radiation other than selected wavelengths after a significant contribution of other wavelengths has been previously removed by a dichroic mirror. The first filter removes all wavelengths other than a first wavelength, and a second filter removes all wavelengths other than a second wavelength. The filtering assembly should also include a rotatable reflective disk positioned in the optical path that directs the radiation.

The rotatable reflective disk includes a notch that covers a portion of the disk less than 180° on the periphery of the disk. During a single rotation of the disk, the notch rotates to a first position that is in line with the path of radiation so that the radiation passes through the notch to the first filter. After exiting the first filter, it is reflected by a back surface of the disk to produce a signal of the first wavelength. A reflector may be positioned to redirect the light so that it reflects off this back surface. The notch also rotates to a second position so that the radiation reflects off a front reflective surface of the disk to pass through the second filter, and subsequently passes through the notch to produce a signal of a second wavelength. Once again, a reflector may be used to direct the light back through the notch after exiting the second wavelength. Between the above noted positions, the notch rotates to positions at which the radiation reflects off the reflective surface of the disk twice resulting no signal being produced.

The system includes a means for synchronizing the detector and the filtering assembly. One of two synchronization strategies may be employed. In the first synchronization strategy the detector dictates the activity of the reflective disk. Specifically, the detector may be a video camera that generates a vertical synchronization signal. This vertical synchronization signal is tied into the power supply of a synchronous motor that drives the reflective disk. Since the synchronous motor activity is determined exclusively by its power supply, the coupling of the vertical synchronization signal to the power supply guarantees that the two will be synchronized.

In the alternate approach, the camera does not dictate the activity of the reflective disk; rather the reflective disk dictates the activity of the camera. A position sensor tells the system where the disk is positioned relative to the optical light path. The position sensor generates signals that are forwarded to the camera that dictate the synchronization of the camera. The result of either approach is that the framing of images by the camera is in synch with the rotation of the disk.

If the microscope system is used to detect the level of calcium in a living cell, it is desirable that the filters operate in the ultraviolet range. Specifically for the calcium indicator, Fura-2 one of the filters should transmit around 340 nanometers and another should transmit 380 nanometers light. Using this waveband of light, the surface of the disk preferably is comprised of a reflective material such as aluminum. Moreover, the camera may be a charge coupled device camera that uses an array of charge coupled devices for imaging.

During each rotation of the reflective disk, it is certain that the light from the light source will experience three steps. First, in a first position, the light passes through the notch and reflects into a light guide that carries the light to its destination. In the second position, the light reflects off the surface of the disk and subsequently, passes through the notch in the disk to the light guide. Between the first and second positions, the light reflects off a disk the first time, and then reflects off the disk a second time so as to not enter the light guide. Given that the rotation of the disk is tied into the framing of the camera during each rotation of the disk, the camera records two frames. Each frame is associated with a corresponding wavelength of light, and the frames are generated in consecutive alternate order until the disk stops rotating. Because the camera utilizes alternate frames to scan entire images, it is desirable to use a camera that operates in a noninterleaving mode.

A single waveguide may be used in the present invention for carrying light to the sample as well as for carrying returning fluorescence generated in response to the excitation of the sample to a sensor. In this embodiment, it is preferred that the single waveguide have a dichroic mirror that distinguishes between excitation signals and the emitted returning fluorescence. Specifically, it is preferred that the excitation signals are reflected by the dichroic mirror and the fluorescence passes through the dichroic mirror. If the waveguide is a coherent fiber optic bundle, a camera may be used to receive the resulting fluorescence. However, if the waveguide is not a coherent fiber optic bundle, a photomultiplier tube should be used.

DETAILED DESCRIPTION OF THE PREFERRED EMBODIMENT

In the preferred embodiment of the present invention a spectrofluorometer device utilizes two different wavelength signals to excite a sample. It should be noted that the basic approach used to excite the sample may also by used to filter the fluorescence generated from the sample. The sample is typically a piece of biological tissue such as a living cell loaded with an appropriate fluorescent indicator substance. The fluorescence that results from the excitation of the sample is viewed by a camera and forwarded to a data processing system for further analysis. The response of the sample to the two distinct excitation signals reveals useful information about the properties of the sample.

Figure 1:
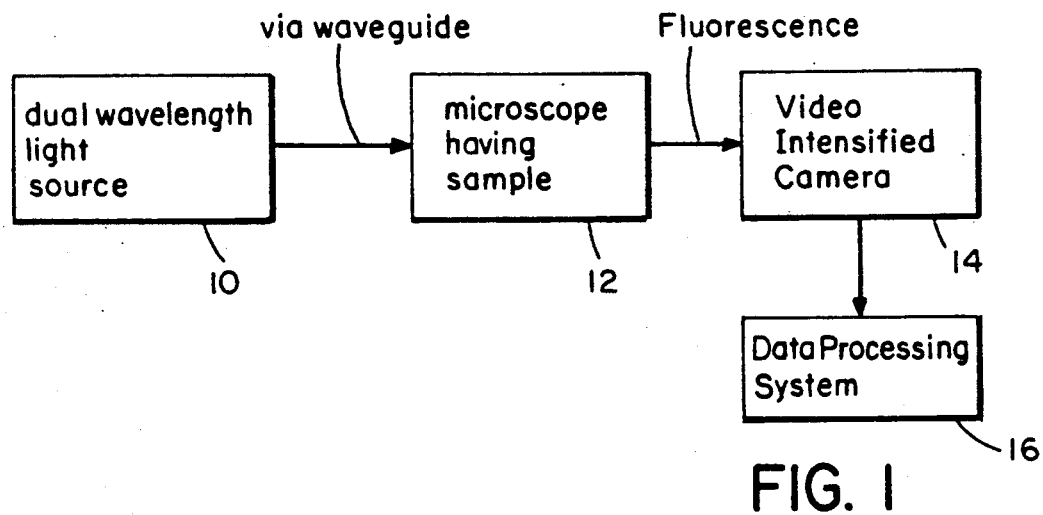
FIG. 1 shows a block diagram of the major components of the spectrofluorometer.

A general overview of the spectrofluorometer system of the preferred embodiment is shown in FIG. 1. In particular, a dual wavelength light source provides excitation signals of two distinct wavelengths. A 350 nanometers excitation signal is provided and a 380 nanometers wavelength excitation signal is also provided for calcium ion measurement with Fura-2. A 350 nanometers excitation signal as opposed to a 340 nanometers excitation signal is used because of the transmission characteristics of the microscope objective of the system. It should be noted that other wavelengths may be used for quantitation of other substances and are intended to be encompassed within the present invention. These excitation signals are produced as pulses in an alternating sequence. They travel via a light guide to a microscope 12 wherein the sample to be excited is located.

The 350 nanometers and 380 nanometers excitation signals are chosen because of the information they reveal with respect to calcium in cells loaded with the calcium indicator substance Fura-2. In particular, the level of calcium in a cell has been shown to be an important indicator of biological activity within a living cell. The concentration of calcium within the living cell can be tracked to monitor activity within the cell. Empirically, it has been shown that the fluorescence produced by exciting a cell at these ultraviolet wavelengths provides useful information concerning spatial and temporal aspects of the calcium concentration within a cell.

The dual wavelength light source 10 is compatible with any inverted mircoscope 12 equipped for epifluorescence. A microscope that may be used is the Zeiss IM35. The excitation signals are focused upon the living cell to generate the fluorescence. The cell is located typically on a slide positioned on the microscope 12. The resulting fluorescence may be viewed via eyepieces situated on the microscope 12. Furthermore, the fluoresence is recorded by a video camera 14 disposed so as to view the fluorescence. Specifically, the image of the fluorescence impinges on an image intensifer that is coupled to the camera 14. The camera 14, in turn, passes the data that it retrieves to a data processing system 16 that may be used to generate a two dimensional image of the concentration of calcium at each point within the cell as monitored over time. The image may be colored so as to indicate different calcium concentration levels.

Figure 2:
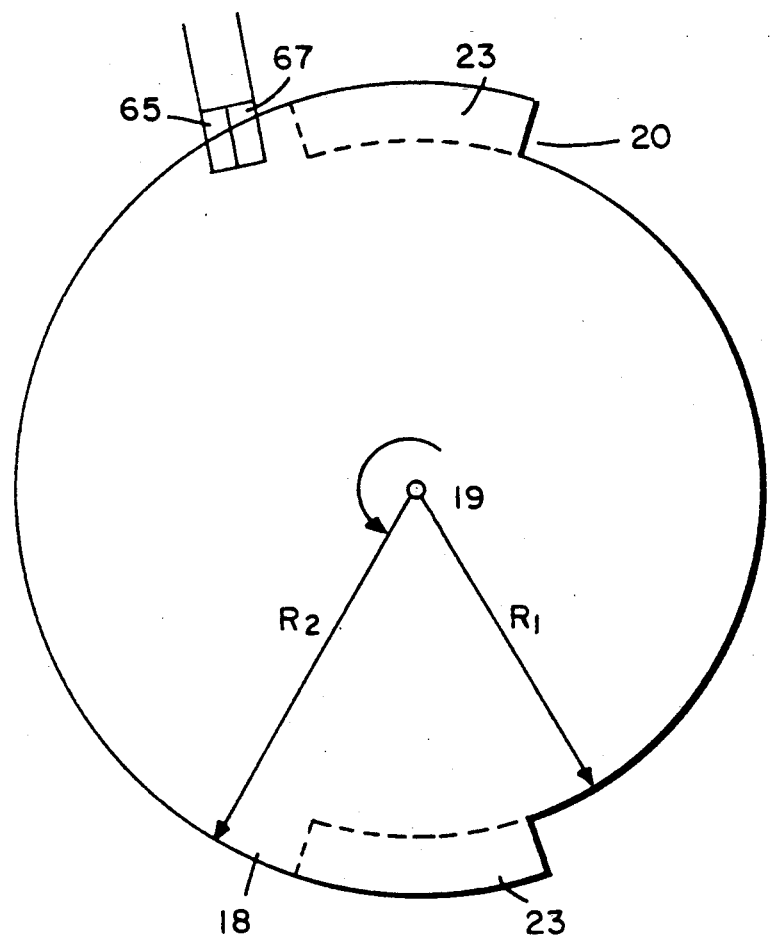
FIG. 2 shows the rotatable reflective disk.

The dual wavelength light source 10 in the preferred embodiment is different from previously used dual wavelength light sources. In particular, it utilizes a reflective disk chopper wheel 18 such as shown in FIG. 2. The chopper wheel disk 18 rotates about an axis 19 in the direction indicated by the arrow in FIG. 2. The disk 18 is comprised entirely of reflective material so that if light impinges upon either surface of the disk 18 it will be reflected. A good choice for a disk material is polycarbonate upon which aluminum may be vaccuum deposited. The disk 18 has a circular notch on one of its halves. A counterweight (not shown) is provided on the same half to allow for balanced rotation.

Figure 3:
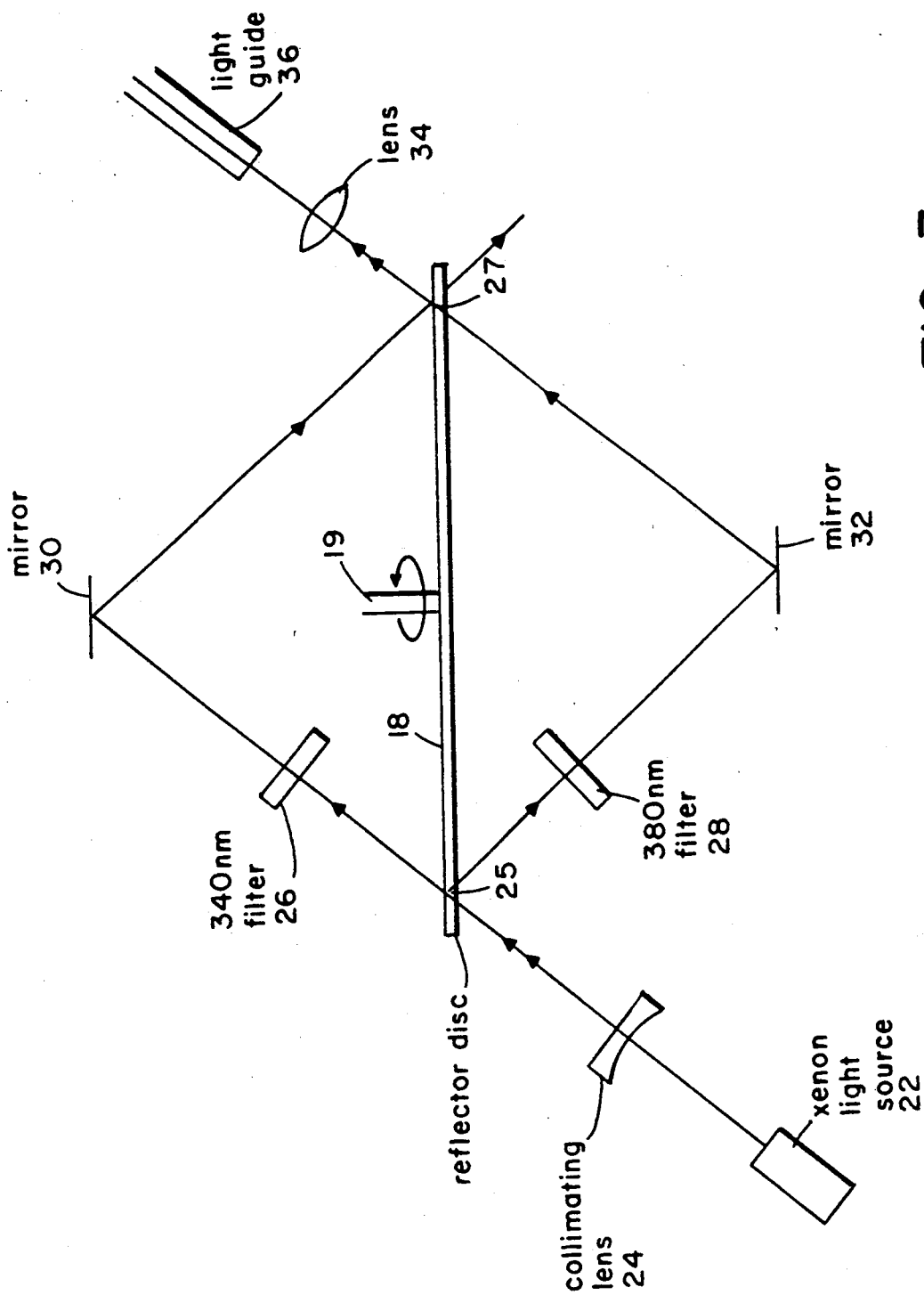
FIG. 3 shows the path of the light when planar mirrors are used.

The apparatus with which disk 18 is used to produce alternating excitation signals of different wavelengths is shown in FIG. 3. To generate the excitation signals a xenon light source 22 such as an arc bulb generates a light signal that is collimated by a collimating lens 24. The resulting collimated light is directed toward the reflective disk 18 at a location between the radii R1 and R2 in FIG. 2. If the reflective disk 18 is rotated so that the reflective surface between R1 and R2 is located at the point 25 where the path of the light signal intersects the reflective disk 18, the light signal is reflected so that it passes through the 380 nanometers interference filter 28. This filter 28 removes all light within the source signal that has a wavelength other than 380 nanometers. The 380 nanometers light signal subsequently proceeds to a planar mirror 32 where it is directed back towards the reflective disk 18. In most instances, the light directed back towards the disk will pass through the notch 20 because the majority of the reflective space on the disk is located opposite the notch 20 on the reflective disk 18. When the light passes through the notch 20 of the disk 18, it enters a quartz lens 34 where it is focused into a light guide 36 that delivers the 380 nanometers excitation signal to the sample.

Suppose on the other hand, that the notch 20 is not located at point 27 but rather at one of the portions of the reflective surface known as dead zones 23 (as indicated by broken line in FIG. 2). In that case, the light exiting the 380 nanometers filter is reflected off t  'sk 18 and does not enter the light guide 36. As such, no excitation signal is provided to the sample.

Another possibility is that the notch 20 is located at position 25. In that case, the collimated light passes the disk 18 to a 350 nanometers interference filter 26. This filter removes out all wavelengths of light in the light signal other than 350 nanometers. The resulting 350 nanometers excitation signal strikes a planar mirror 30 where it is directed back towards the opposite edge of the reflective disk 18. When the notch is located at position 25, it is certain that a reflective surface is located at position 27 and thus, the resulting 350 nanometers excitation signal is certain to be reflected back into the quartz lens 34 and directed into the light guide 36.

The positioning of the dead zones 23 assures that there will be a gap in which no excitation signal is generated at each transition between the 380 nanometers wavelength excitation signal and the 350 nanometers excitation signal. Hence, during one rotation it is certain that there are four events. First, a 350 nanometers excitation signal enters the light guide 36. Second, there is a gap in which no excitation signal is produced. Third, a 380 nanometers excitation signal is produced, and fourth, there is another gap in which no excitation signal occurs. These gaps provide a period of relief in which a definite transition between the two wavelengths of excitation signals can be discerned. Because the dead zones are at least as wide as the beam of light, there is never a time when the sample is illuminated by both wavelengths.

Figure 4:
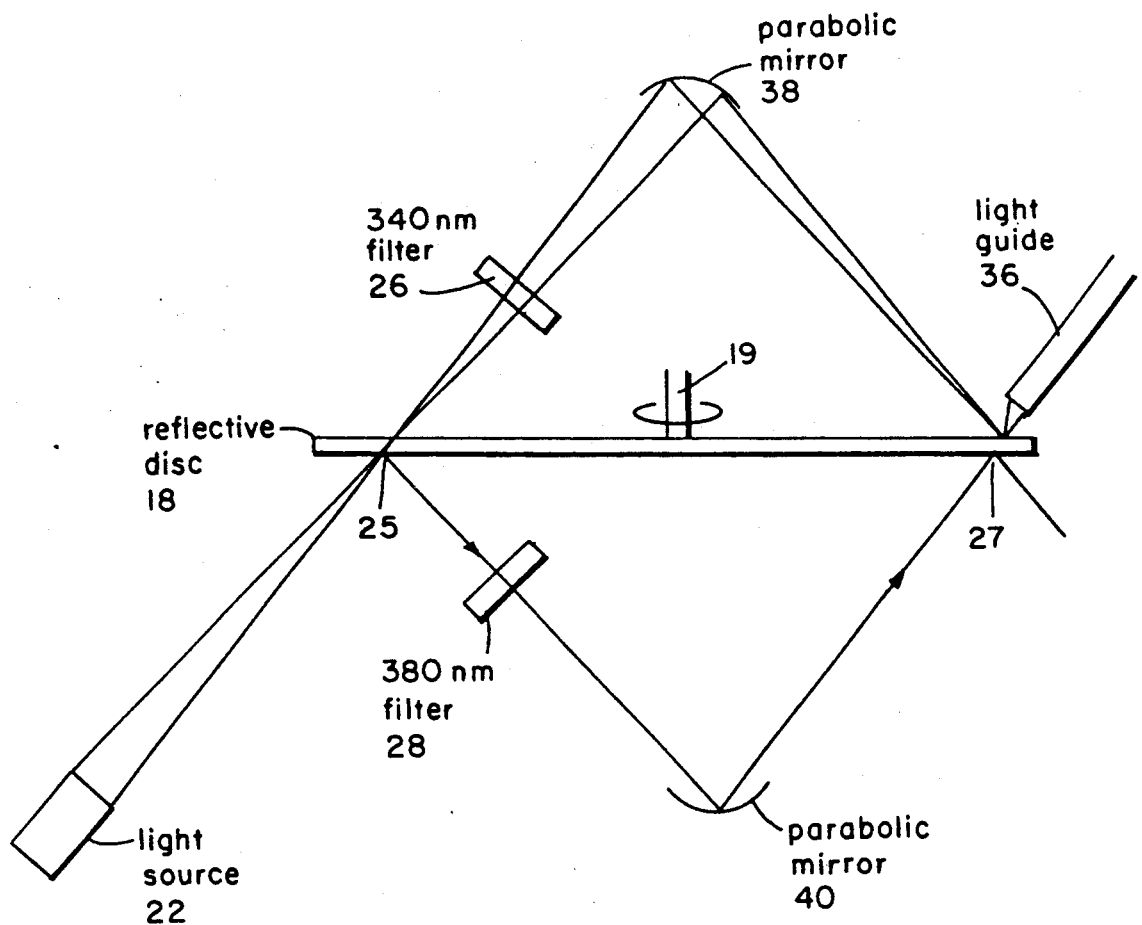
FIG. 4 shows the path of the light when off-axis-parabolic mirrors are used.

FIG. 3 depicts the mirrors 30 and 32 as planar mirrors. Other types of mirrors, however, may be used. For instance, as shown in FIG. 4 off axis parabolic mirrors 38 and 40 may be substituted for the planar mirrors 30 and 32. The light source is inherently converging and can be positioned so that its focal point is at the disk 18. The parabolic mirrors 38 and 40, in turn, focus the light at a secondary focal point 27. Because they are focused in this manner, the light beams once again focus at the disk at position 27 when they are reflected by the parabolic mirrors 38, 40. This focusing eliminates the need for a quartz lens 34 to focus the light into a light guide 36 because the light guide 36 can be positioned sufficiently near to the reflective disk 18 where it is assured that the light reflecting off the disk 18 will enter the light guide 36 because of the minimal divergence of the signal relative to light guide. Moreover, the focusing of the signal at the disk 8 reduces the surface area necessary for the dead zones 23. This reduction in surface area requirements is attributable to the assured minimal area that the light will strike given that the area of striking is near a focal point.

The alternating excitation signals having wavelengths of 380 nanometers and 350 nanometers, respectively, enter the waveguide 36 destined for the sample. The resulting fluorescence of the sample when the excitation signal excites the sample is captured by a video camera 14 that observes the sample. The video camera 14 records a single snapshot (video frame) of the fluorescence produced from excitation of the sample for each alteration of the excitation signals. In other words, for a single rotation of the disk 18 the camera 14 takes two frames: one corresponds to the fluorescence produced by the 350 nanometers excitation signal, and the other corresponds to the fluorescence produced by the 380 nanometers excitation signal. If the fluorescence attributable to the 350 nanometers excitation signal is designated as $\lambda_1$ and the fluorescence attributable to the 380 nanometers excitation signal is denoted as $\lambda_2$. The sequence of snapshots that the camera takes resembles those shown in FIG. 5.

Figure 6A:
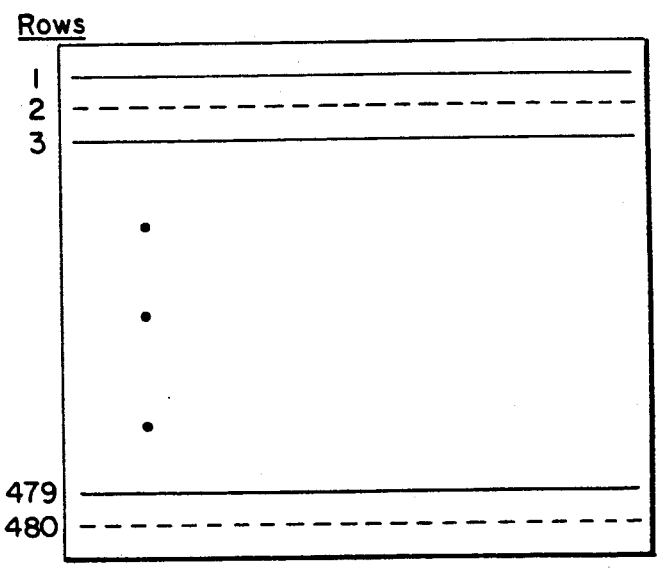
FIG. 6a, 6b and 6c show the typical video camera pixel array and the framing of such pixels.
Figure 6B:
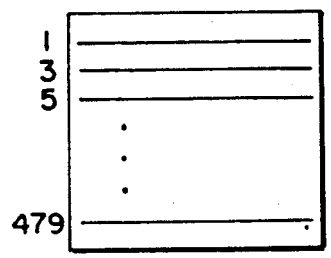
Figure 6C:
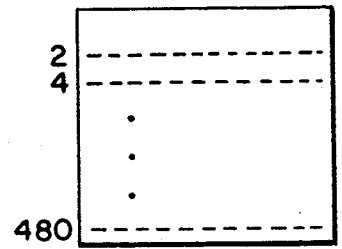

Typical video technology is designed so that 480 rows of pixels are scanned for each image that is viewed. However, due to the state of technology when the pioneering work was done in the video technology field, the entire 480 rows of pixels are not typically read in consecutive sequential order. Instead, an approach has evolved where the odd numbered rows and the even numbered rows are read alternately to produce one "interlaced" frame. Thus, FIG. 6a represents a typical video imaging array of 480 rows of pixels. The odd numbered rows are designated by solid lines, and the even numbered rows are designated by dotted lines. To scan the entire 480 rows of the imaging array, the rows of pixels are first read as a single field in the sequence shown in FIG. 6b (i.e. all the odd rows are read). Subsequently, the even numbered rows are read as a second field as shown in FIG. 6c. When both odd and even rows are displayed alternately a single interlaced image is produced. To facilitate such an approach, a signal known as an odd-field synchronization signal was developed. It indicates the initiation of the two passes through the respective odd and even rows of the imaging array. Typically, the odd-field synchronization signal is issued at a rate of 30 Hz, and the vertical synchronization signal is at a rate of 60 Hz.

Figure 7:
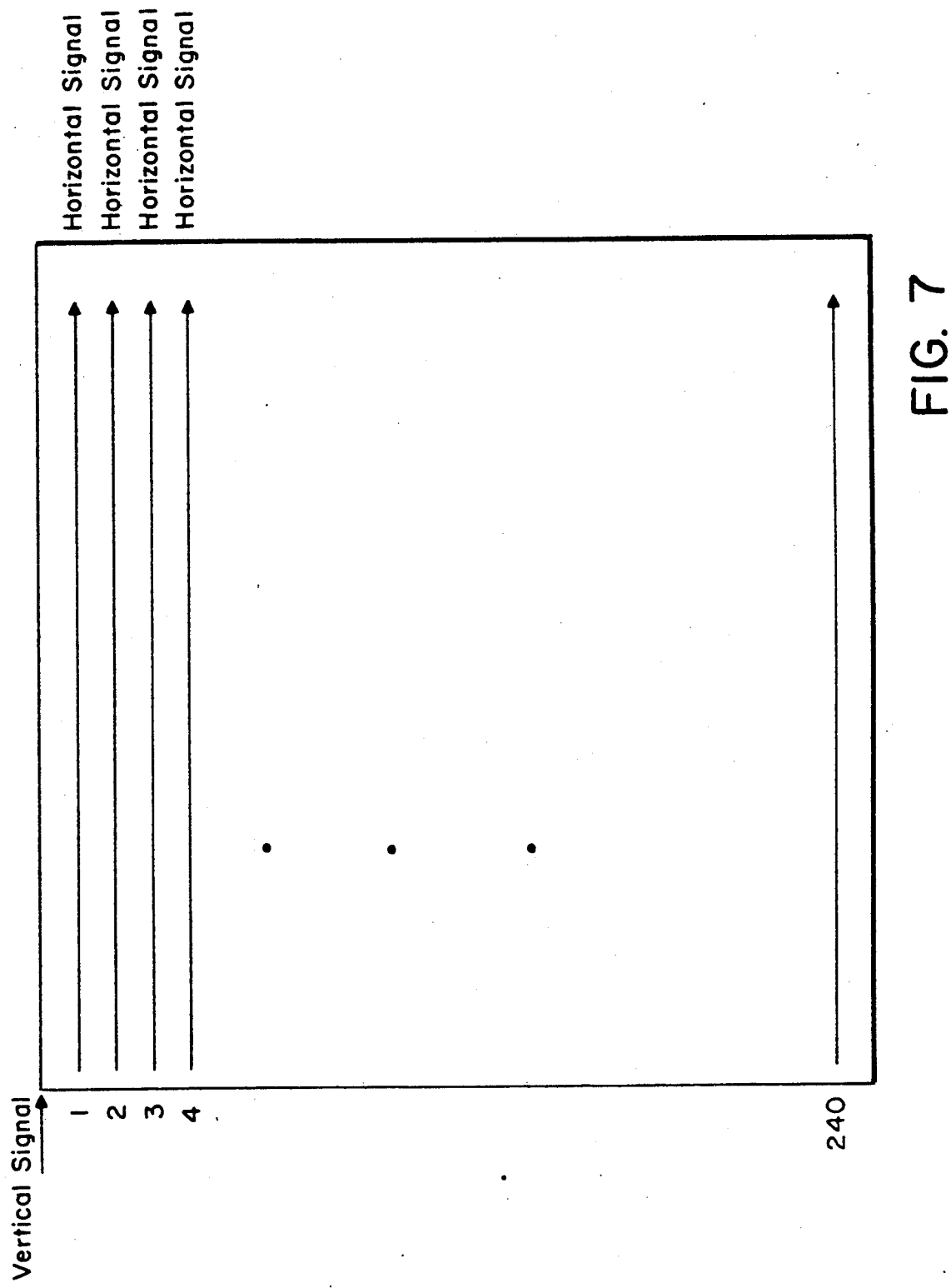
FIG. 7 shows the imaging array of the preferred embodiment.

The preferred embodiment utilizes an integrated circuit camera 14 that is configured as 240 double rows of pixels. The imaging array of the camera 14 is comprised of a series of charge coupled detector elements (CCDs). In a CCD camera all pixels sample the image simultaneously for the same amount of time in parallel. The light impinging on each pixel is stored as an analog signal that is integrated over the frame exposure time. In the present application this property tends to minimize errors due to intensity fluctuations in the light source. In a mode of operation utilized with the present system, the CCDs are configured so that the signals on adjacent pairs of rows is automatically added. Thus, the signal of the first pixel in row 1 is automatically added to the signal of the first pixel in row 2. Moreover, the second CCD element in row 1 is automatically added with the second element in row 2, and so on. The net result of this approach is that the entire image that is received by the array is output as 240 rows of pixels such as shown in FIG. 7 at a frame rate of 60 Hz. The alternating frames are identical double pixels, not alternating even and odd pixels.

Figure 5:
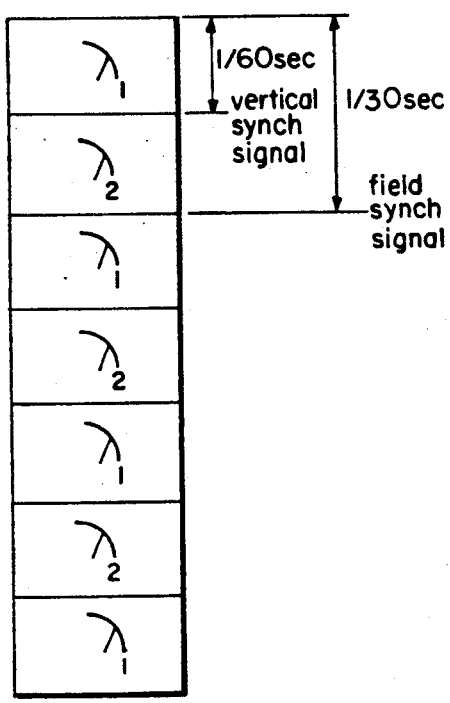
FIG. 5 shows a sequence of alternating video frames.

The major benefit of this approach is that entire images may be received every sixtieth of a second as opposed to every thirtieth of a second. Instead of merely looking at alternate portions of a single image in two consecutive fields, the preferred embodiment looks at two different images in consecutive fields. Hence, as shown in FIG. 5 every sixtieth of a second the fluorescence produced by one of the excitation signals is viewed, and every thirtieth of a second both florescent images have been recorded.

The camera 14 is synchronized by three synchronization signals. Specifically, a horizontal signal is used to synchronize the scanning of rows of pixels. More particularly, a horizontal signal is produced to synchronize the initiation of scanning an entire row of the image array as shown in FIG. 7 for rows 1, 2, 3, and 4. A vertical synchronization signal, however, is produced only when all of the rows of the array have been scanned (note the vertical signal at row 1 in FIG. 7). The third synchronization signal, the odd field synchronization signal has already been discussed. It is produced with every other vertical synchronization signal.

Figure 8A:
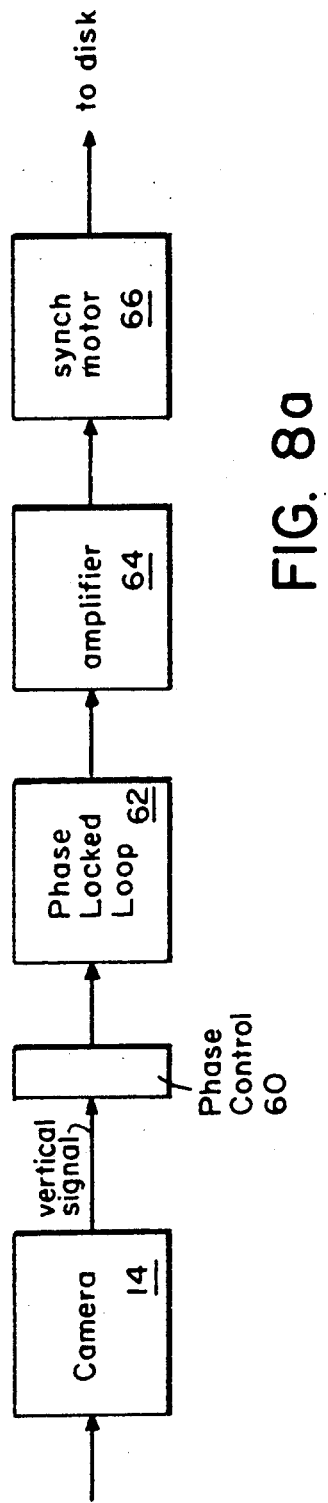
FIG. 8a and 8b show block diagrams of alternate synchronization approaches.

In accordance with one approach, the camera 14 uses its synchronization signals to control operation of a synchronous motor 66 that regulates the rotation of disk 18. A synchronous motor has the property of maintaining a fixed phase relationship to the sinusoidal power signal that drives it. The basic configuration is depicted in FIG. 8a. The vertical synchronization signal is sent by the camera 14 to a phase control circuit 60. The phase control circuit is used to insert a user controllable delay before the vertical signal is forwarded to a phase locked loop 62. The phase control circuit 60 is typically adjusted when the system is first turned on so as to adjust the phase between the camera's framing and the rotation of the disk. The circuit 60 is a one shot device that aligns the two processes to guarantee that they are in synch. The phase locked loop 62 generates a low voltage 60 Hz sinusoidal output. This output is amplified by an amplifier 64 to produce an 115 RMS, 60 Hz signal that provides power to the synchronous motor 66 to drive the disk.

A light source (photodiode) 65 and light detector (photo-transistor 67) are positioned near the periphery of the disk 18 so that the system detects what part of disk 18 is currently in the light patch. This position sensor mechanism 65 and 67 is used along with the vertical synchronization pulses to make certain that the disk 18 and camera are synchronized. Specifically, both can be observed on an oscilloscope to make certain they are aligned.

Figure 8B:
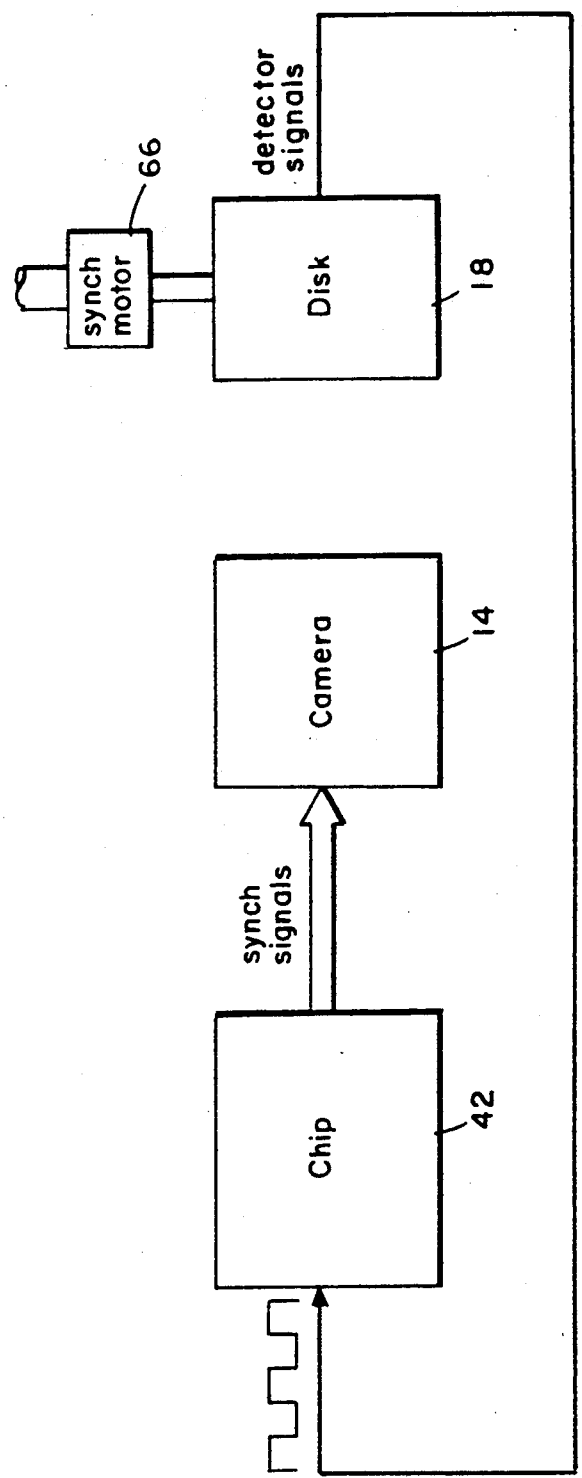

Still another approach to synchronization is depicted in FIG. 8b. Instead of the camera 14 dictating the activity of the motor 66, the motor 66 dictates the activity of the camera 14. For this approach, the reflective disk 18 is provided with a light source-detector assembly (65, 67) situated in the transition between the notch and the reflective surface area (i.e. the dead zones 23). When the detector is struck by the light produced from the photodiode 65, the system can be assured that a new excitation signal is being initiated. The resulting signal generated by the detectors is a step function similar to that shown in FIG. 8b. The step function enters a synchronization signal generator integrated circuit chip 42 that generates video synchronization signals in response to the step functions. The synchronization signals from the chip 42 enter camera 14 and dictate the scanning activity of the camera 14. The advantage of this approach is that the synchronous motor can be driven directly by 60 Hz line voltage. There is no requirement for the expensive phase locked loop and power amplifier circuit of FIG. 8a.

Figure 9:
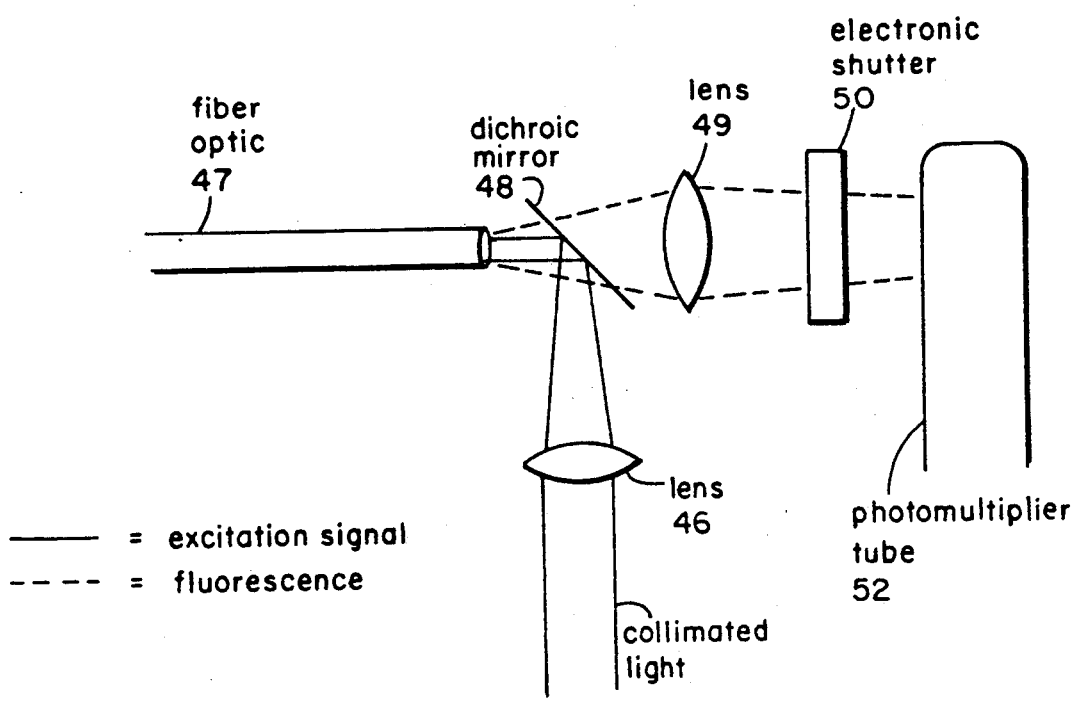
FIG. 9 shows a single waveguide used for carrying both the excitation and the fluorescence.

Another unique feature of the present invention, particularly in a nonimaging application, is that a single waveguide may be used both for transmitting the excitation signal to the sample as well as for receiving the returning fluorescence from the sample. FIG. 9 depicts the design used for this single waveguide. In particular, a collimated excitation signal of either of the specified wavelengths generated from the dual wavelength light source passes through a lens 46. It is then directed to a dichroic mirror 48. The dichroic mirror 48 transmits light having wavelengths greater than 430 nm. Because of the short wavelength of the excitation signals (i.e. 350 nanometers and 380 nanometers), the dichroic mirror 48 reflects the excitation signal to a fiber optic 47 that carries the signal to the sample As previously discussed, the sample produces fluorescence. The resulting fluorescence is emitted as a diverging beam by the light guide and travels back towards the dichroic mirror 48. The fluorescence emission of Fura-2 resides in a wave band near 500 nm and hence, passes through the dichroic mirror. A barrier filter (not shown) may be used to remove undesirable wavelengths that remain in the fluorescence after the dichroic mirror 48. Having passed through a dichroic mirror 48, the fluorescence beam is collimated by a lens 49 and travels to an electronic shutter 50. When the shutter 50 is opened the fluorescence strikes upon a photomultiplier tube 52. The photomultiplier tube 52 translates the fluorescence intensity into electrical signals that can be analyzed by the data processing system 16. A single output signal rather than a video frame is obtained for each excitation. The disk position sensor output is used by the data processing system 16 to synchronize the data retrieval from the photomultiplier tube. In the alternative, a video camera 14 could replace the photomultiplier tube if a coherent fiber optic bundle were used.

The present invention provides several benefits for spectrofluorometry. First, it provides alternating pulses of excitation signals in an efficient manner. Moreover, it does not require expensive circuitry, and it makes certain that the camera and the excitation signals are in synchronization. In addition, it can be implemented with lower cost than many current systems and can readily be adjusted to provide different wavelengths of light by easily changing the filter. It, likewise, allows for clean recombination of the light signal without losses incurred by the use of a conventional optical beam splitter.

While the invention has been particularly shown and described with reference to preferred embodiment thereof, it will be understood by those skilled in the art that various changes in form and details may be made without departing from the spirit and scope of the invention as defined in the appended claims. For instance, a rotating filter may be used rather than a reflective disk. Moreover, the filters could be placed at the receiving end of the system so as to filter the fluorescence into alternating frames. Still further, the principles and components discussed above have equal utility for a spectrophotometer as well as for a spectrofluorometer.

I claim:
1. A microscope system comprising:
 a) a means for locating a sample;
 b) a source of radiation for illuminating the sample;
 c) a detector for detecting radiation from the sample resulting from illumination;
 d) a filtering assembly in the optical path of the radiation, the filtering assembly comprising a first filter and a second filter for removing all wavelengths from the radiation other than a first wavelength and a second wavelength, respectively; said filtering assembly further comprising a rotatable reflective disk positioned in the optical path wherein said disk has a notch that covers a portion of the disk less than 180° of a periphery of the disk, and wherein during a single rotation of the disk the notch rotates to a first position in line with the path of the radiation so that the radiation passes through the notch to the first filter and is reflected by a back surface of the disk to produce a signal of the first wavelength, and the notch rotates to a second position so that the radiation reflects off a front reflec- tive surface of the disk to pass through the second filter and through the notch to produce a signal of the second wavelength, and the notch also rotates to a position so that the radiation reflects off the reflective surface of the disk twice so that no signal is produced; and e) a means for synchronizing the detector and the filtering assembly.

2. A microscope system as recited in claim 1 wherein the filtering assembly is positioned in the optical path between the source of radiation and the sample.

3. A microscope system as recited in claim 1 wherein the filtering assembly is positioned in the optical path between the sample and the detector.

4. An apparatus for generating a dual wavelength excitation signal for a spectrofluorometer, comprising:

a) a light source for generating light;

b) a first filter for filtering the light generated by the light source so as to allow light only of a first wavelength to pass through the first filter;

c) a second filter for filtering the light generated by the light source so as to allow light only of a second wavelength to pass through the second filter; and d) a rotatable reflective disk positioned in a path of the light from the light source as well as between the first filter and the second filter; said disk having a notch that covers a portion of less than 180° of a periphery of the disk, wherein during a single rotation of the disk, the notch rotates to a first position in line with the path of the light so that the light passes through the notch to the first filter and is reflected by a back surface of the disk to produce an excitation signal of the first wavelength, and the notch rotates to a second position so that the light reflects off a front reflective surface of the disk to pass through the second filter and then through the notch to produce an excitation signal of the second wavelength, and the notch also rotates to a position so that the light reflects off the reflective surface of the disk twice so that no excitation signal is produced.

5. An apparatus as recited in claim 4 wherein the light source is an ultraviolet light source.

6. An apparatus as recited in claim 4 wherein the light source is a xenon light source.

7. An apparatus as recited in claim 4 wherein one of the two filters only allows light of approximately 350 nanometers to pass.

8. An apparatus as recited in claim 4 wherein one of the two filters only allows light of approximately 380 nanometers to pass.

9. An apparatus as recited in claim 4 wherein the reflective disk is comprised of polycarbonate coated with aluminum.

10. An apparatus as recited in claim 4 further comprising a synchronous motor for driving the reflective disk.

11. An apparatus as recited in claim 4 wherein rotation of the reflective disk is synchronized with a camera that detects excitation of the sample so that excitation resulting from alternating wavelength excitation signals appear in alternating video frames.

12. An apparatus as recited in claim 11 wherein the camera is a charge coupled detector camera.

13. An apparatus as recited in claim 4 further comprising a synchronous motor that drives the reflective disk.

14. An apparatus as recited in claim 13 wherein video synchronization signals of the camera dictate the rotation produced by the synchronous motor.

15. An apparatus as recited in claim 14 wherein the video synchronization signals are used to generate the power signal to the synchronous motor.

16. An apparatus as recited in claim 13 further comprising a position sensor for sensing the position of the disk relative to the optical path.

17. An apparatus as recited in claim 16 wherein signals generated by the position sensor determine the video synchronization signals of the camera.

18. A method of generating a dual wavelength excitation signal for a spectrofluorometer using a rotatable reflective disk, a light source focused on an edge of the disk, and a first and a second filter, comprising the steps of:

a) rotating the disk so that light from the light source passes through a notch in the disk to the first filter and is returned to be reflected by a back surface of the disk to produces an excitation signal of a first wavelength;

b) rotating the disk so that the light from the light source strikes a reflective surface of the disk rather than the notch and reflects the light so that it passes through the second filter and is returned through the notch to produce an excitation signal of a second wavelength; and c) rotating the disk so that light from the light source strikes a reflective surface of the disk twice and reflects so as to produce no excitation signal.

19. A lighting system for a spectrofluorometer, comprising:

a) a light source for generating a light signal;

b) a first and a second filter, each for filtering the light signal from the light source to remove all wavelengths in the light other than a first and a second wavelength, respectively;

c) a rotatable reflective disk positioned in a path of the light signal generated by the light source for directing light produced by the light source, said disk having a notch in a portion less than 180° of the disk, a first reflective surface on another portion of the disk and a second reflective surface shared by both halves of the disk, wherein the disk rotates such that during a portion of each rotation the notch rotates to a position in line with the path of the light signal so that the light signal passes through the notch onto the first filter to generate an excitation signal of a first wavelength, and during a different portion of each rotation, the first reflective surface rotates to a position in line with the path of the light signal so that the light signal is directed through a second filter to generate an excitation signal of a second wavelength, and during a final portion of each rotation, the second reflective surface rotates to a position in line with the path of the light signal so that the light signal passes though the second filter to generate an excitation signal of the second wavelength;

d) a waveguide for receiving the excitation signals from the first filter and the second filter;

e) a first reflector for directing the first excitation signal so that it reflects off a reflective surface of the disk into the waveguide;

f) a second reflector for directing the excitation signal of the second wavelength through the notch to the waveguide if the excitation signal was produced from a light signal that reflected off the first reflective surface and for, otherwise, directing the excitation signal of the second wavelength to the second reflective surface so that the waveguide receives no excitation signal.

20. A lighting system as recited in claim 19 wherein the light source is an ultraviolet light source.

21. A lighting system as recited in claim 20 wherein the light source is a xenon light source.

22. A lighting system as recited in claim 19 wherein one of the two filters only allows light having a wavelength of approximately 350 nanometers to pass.

23. A lighting system as recited in claim 19 wherein one of the two filters only allows light having a wavelength of approximately 380 nanometers to pass.

24. A lighting system as recited in claim 19 wherein the reflective disk is made of polycarbonate coated with aluminum.

25. A lighting system as recited in claim 19 wherein the first reflector and the second reflector are mirrors.

26. A method of providing dual wavelength lighting for a spectrofluorometer, comprising the steps of:
   a) shining a light signal from a light source onto a rotatable reflective disk;
   b) rotating the disk so that the light signal passes through a notch into a first filter that filters out all wavelengths of light other than a first wavelength;
   c) directing the light signal after it passes through the first filter so that it reflects off the disk into a waveguide;
   d) rotating the disk again so that the light signal reflects off a first reflective surface of the disk into a second filter that filters out all wavelengths of light other than a second wavelength;
   e) directing the light signal after it passes through the second filter so that it passes through the notch to the waveguide;
   f) rotating the disk again so that the light signal reflects off a second reflective surface of the disk so that it passes through the second filter; and
   g) directing the light signal after it passes through the second filter so that it reflects off the disk and fails to enter the waveguide.

27. A method as recited in claim 26 wherein steps a-g are repeated for each rotation of the disk.

28. A method as recited in claim 26 wherein the directing steps comprise reflecting the light signal using mirrors.

29. A spectrometer comprising: 'a) a dual wavelength lighting system that generates excitation signals of two unique wavelengths in an alternating sequence, said lighting system including a rotatable disk that directs a light signal from a light source by rotating to determine which wavelength excitation signal is produced wherein the disk has a first portion that directs the light signal so that a first unique wavelength excitation signal is produced when the light signal strikes the first portion of the disk, and the disk also has a second portion that directs the light signal so that a second unique wavelength excitation signal is produced;
   b) an imager for imaging fluorescence produced when the sample is excited by the excitation signals, said imager receives alternating snapshots of fluorescence generated in response to the alternating sequence of excitation signals of unique wavelength and is synchronized with the rotatable disk; and
   c) a synchronizing circuit connected to the rotatable disk and the imager that generates synchronization signals so as to synchronize the rotation of the disk and the imaging by the imager such that the imager provides fluorescence images corresponding to the alternating excitation signals in consecutive video frames.

30. A spectrofluorometer as recited in claim 29 wherein the light source is an ultraviolet light source.

31. A spectrofluorometer as recited in claim 29 wherein the light source is a xenon light source.

32. A spectrofluorometer as recited in claim 29 wherein the imager is an array of charge coupled devices.

33. A spectrofluorometer as recited in claim 29 wherein the imager is a camera that generates video synchronization signals that are tied into a power source of a synchronous motor that rotates the disk so as to synchronize the framing of the camera and rotation of the disk.

34. A spectrofluorometer as recited in claim 33 wherein the video synchronization signal comprises a vertical synchronization signal produced by the camera after all pixels in the camera have been scanned.

35. A spectrofluorometer as recited in claim 34 wherein the camera scans all of its pixels during the interim between successive vertical synchronization signals by averaging the pixel values of adjacent rows of pixels.

36. A spectrofluorometer as recited in claim 34 wherein the vertical synchronization signal is issued every sixtieth of a second.

37. A spectrofluorometer as recited in claim 29 further comprising a data processing system for processing image data received by the camera.

38. A spectrofluorometer as recited in claim 29 wherein the wavelength of the excitation signals alternates at the video frame rate.

39. A spectrofluorometer as recited in claim 29 wherein the disk comprises a reflective disk having a notch.

40. A spectrofluorometer as recited in claim 29 further comprising:
   detector means for detecting angular position wherein the synchronizing circuit is connected to the detector means for providing synchronization signals to the imager so as to synchronize the imaging at the imager with the rotation of the disk to allow the imager to image fluorescence of alternating excitation signals in consecutive video frames.

41. A spectrofluorometer comprising:
   a) a light source for generating light;
   b) an imager for viewing fluorescence of a sample produced when the sample is excited by light from the light source; and
   c) a single waveguide for carrying light to the sample to excite the sample and for returning fluorescence generated in response to the light to the imager.

42. A spectrofluorometer as recited in claim 41 wherein the single waveguide has a dichroic mirror that distinguishes between the excitation signals and the emitted returning fluorescence.

43. A spectrofluorometer as recited in claim 41 wherein the excitation signals are reflected by the dichroic mirror, and the flouresence passes through the dichroic mirror.

44. A spectrofluorometer as recited in claim 41 wherein the waveguide comprises a coherent fiber optical bundle.

45. A spectrofluorometer as recited in claim 44 wherein the imager comprises a camera.

46. A spectrofluorometer as recited in claim 41 wherein the imager comprises a photomultiplier tube.

47. A spectroflourometer comprising:
  a) a dual wavelength lighting system that generates excitation signals of two unique wavelengths in an alternating sequence, said lighting system including a rotatable disk that directs a light signal from a light source by rotating to determine which wavelength of excitation signal is produced wherein said disk having a first portion that directs the light signal so that a first unique wavelength excitation signal is produced when the light signal strikes the first portion of the disk, and the disk also has a second portion that directs the light signal so that a second unique wavelength excitation signal is produced, and further, said disk has detectors that situated between the first portion and second portion of the disk that are activated when the light signal strikes the detectors;
  b) a waveguide for carrying the excitation signals to a sample to be excited;
  c) a camera for imaging fluorescence produced when the sample is excited by the excitation signals, said camera receives alternating snapshots of fluorescence generated in response to the alternating sequence of excitation signals of unique wavelengths;
  d) an integrated circuit connected to the detectors that generates synchronization signals to the camera so as to synchronize the imaging at the camera with the rotation of the disk to allow the camera to image flouresence of alternating excitation signals in consecutive video frames.

* * * * *